US009566819B2

(12) United States Patent
McDowell

(10) Patent No.: US 9,566,819 B2
(45) Date of Patent: Feb. 14, 2017

(54) WRITING INSTRUMENT STORAGE AND SANITIZATION APPARATUS

(71) Applicant: Kenneth Vernon McDowell, Rohnert Park, CA (US)

(72) Inventor: Kenneth Vernon McDowell, Rohnert Park, CA (US)

(*) Notice: Subject to any disclaimer, the term of this patent is extended or adjusted under 35 U.S.C. 154(b) by 0 days.

(21) Appl. No.: 14/851,698

(22) Filed: Sep. 11, 2015

(65) Prior Publication Data
US 2016/0207347 A1    Jul. 21, 2016

Related U.S. Application Data

(60) Provisional application No. 62/103,897, filed on Jan. 15, 2015.

(51) Int. Cl.
*B43K 31/00* (2006.01)
(52) U.S. Cl.
CPC ..................... *B43K 31/00* (2013.01)
(58) Field of Classification Search
CPC ..................................... B43K 31/00
See application file for complete search history.

(56) References Cited

U.S. PATENT DOCUMENTS

| | | |
|---|---|---|
| 6,039,928 A | 3/2000 | Roberts |
| 2004/0025899 A1 | 2/2004 | Pinsky |
| 2009/0148358 A1 | 6/2009 | Wind |
| 2009/0314956 A1 | 12/2009 | Long |
| 2014/0245866 A1 | 9/2014 | Hadlock et al. |

*Primary Examiner* — Gene Crawford
*Assistant Examiner* — Ayodeji Ojofeitimi

(57) ABSTRACT

An automated writing instrument storage apparatus designed to receive, sanitize and dispense a writing instrument includes a housing member with a top face having a slot to permit the writing instrument to pass through, a support assembly disposed within the housing member and having a transparent tubular member generally aligned with the housing member slot to receive the writing instrument, an ultraviolet lamp disposed within the housing member and able to direct light generated by the lamp through the transparent tubular member to sanitize the writing instrument stored therein, and a motor assembly disposed within the housing member and operably connected to the support assembly. The motor assembly activates to permit the sanitized writing instrument to slide within the transparent tubular member and through the slot of the housing member, thereby dispensing the sanitized writing instrument to a user.

9 Claims, 5 Drawing Sheets

WRITING INSTRUMENT STORAGE AND SANITIZATION APPARATUS

RELATED APPLICATION

The application claims priority to provisional patent application U.S. Ser. No. 62/103,897 filed on Jan. 15, 2014, the entire contents of which is herein incorporated by reference.

BACKGROUND

The embodiments herein relate generally to writing instruments and methods and/or devices for sanitizing them.

Writing instruments such as pens and pencils are offered and used by many individuals at public locations such as doctor's offices, banks, pharmacies, restaurants, other retail establishments, and the like. With the increasing concern for contagious illnesses and diseases such as the common cold, influenza and Ebola, there exists a need to disinfect these writing instruments to remove any germs, bacteria and/or microorganisms present thereon. Currently, individuals are required to wipe these writing instruments with disinfectant wipes and/or hand sanitizer solution prior to each use. This process is burdensome and impractical.

As such, there is a need in the industry for an automated writing instrument storage apparatus that easily and effectively sanitizes multiple writing instruments at any given time.

SUMMARY

An automated writing instrument storage apparatus configured to receive, sanitize and dispense a writing instrument with enhanced efficiency and reduced user effort is provided. The storage apparatus comprising a housing member comprising a top face, a bottom face and side faces, the top face comprising a slot sufficiently large to permit the writing instrument to pass therethrough, a support assembly disposed within the housing member and comprising a transparent tubular member generally aligned with the slot in the top face of the housing member and configured to receive the writing instrument, an ultraviolet lamp disposed within the housing member and configured to direct light generated by the lamp through the transparent tubular member to sanitize the writing instrument stored therein, and a motor assembly disposed within the housing member and operably connected to the support assembly, wherein the motor assembly is configured to activate to permit the sanitized writing instrument to slide within the transparent tubular member and through the slot of the housing member, thereby dispensing the sanitized writing instrument to a user.

In certain embodiments, the support assembly comprises a rotatable base member configured to store a plurality of transparent tubular members, each transparent tubular member in the plurality of transparent tubular members configured to align with the slot in the housing member to receive one of a plurality of writing instruments. In certain embodiments, a second motor assembly is disposed within the housing member and is configured to adjust the rotatable base member to permit the plurality of writing instruments stored within the transparent tubular members to be exposed to light from the ultraviolet lamp. The second motor assembly is configured to rotate the rotatable base member to align any one of the plurality of transparent tubular members with the slot in the housing member.

BRIEF DESCRIPTION OF THE FIGURES

The detailed description of some embodiments of the invention will be made below with reference to the accompanying figures, wherein the figures disclose one or more embodiments of the present invention.

DETAILED DESCRIPTION OF CERTAIN EMBODIMENTS

Figure 1:
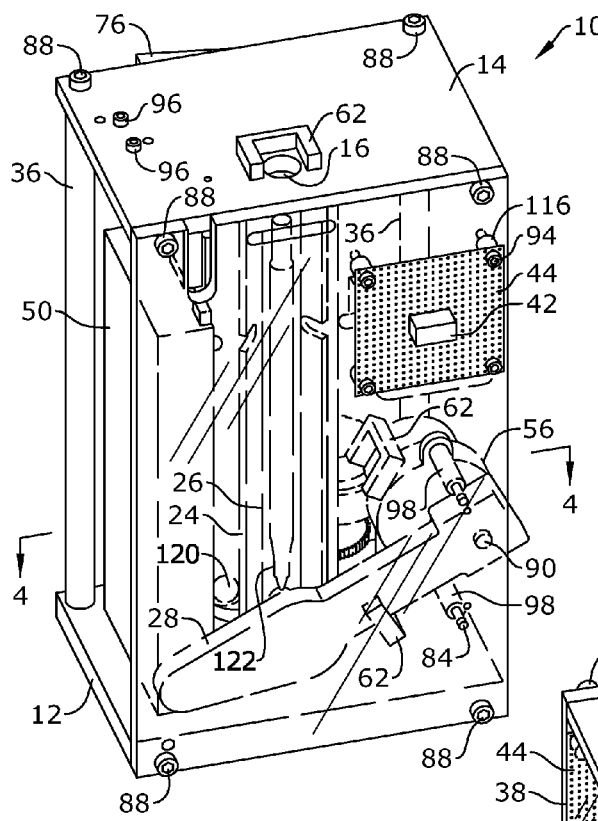
FIG. 1 depicts a front perspective view of certain embodiments of the writing instrument storage apparatus shown in use.
Figure 2:
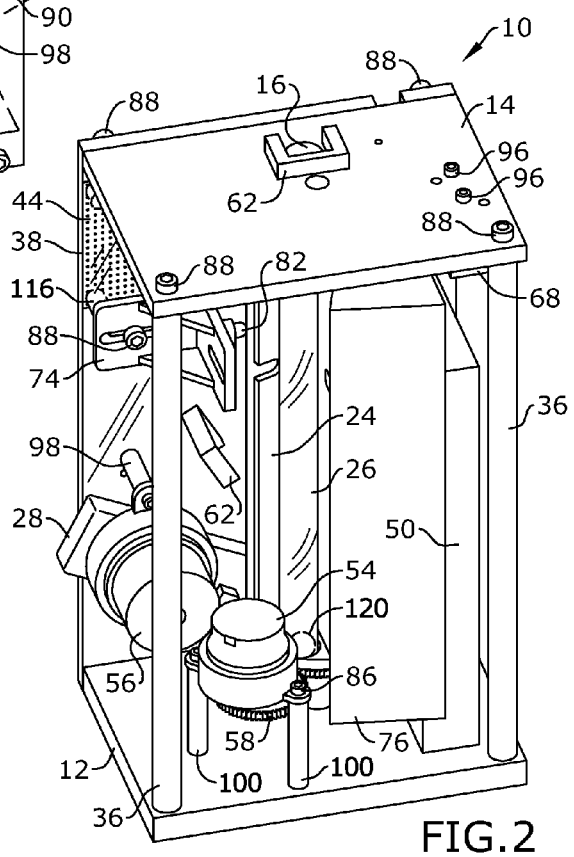
FIG. 2 depicts a rear perspective view of certain embodiments of the writing instrument storage apparatus.
Figure 3:
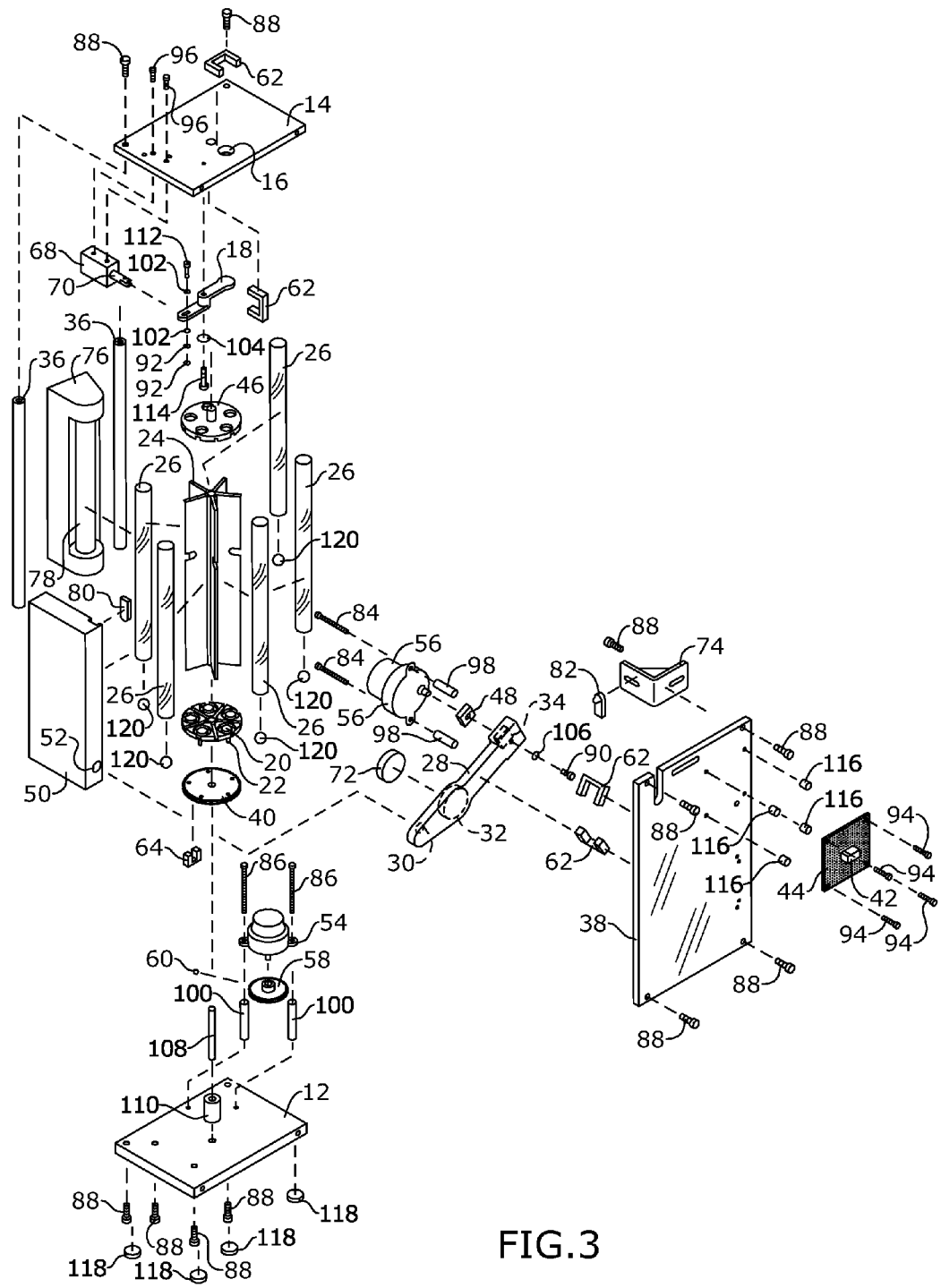
FIG. 3 depicts an exploded perspective view of certain embodiments of the writing instrument storage apparatus.

As depicted in FIGS. 1-3, writing instrument storage apparatus 10 is configured to store, sanitize and dispense a plurality of writing instruments 122. The apparatus is an automated apparatus that enables a hands-free operation. Each writing instrument 122 may include, but is not limited to, pens, pencils, markers, highlighters, or the like. Writing instrument storage apparatus 10 generally comprises a housing having top plate 14, side plate 38 and base plate 12, transparent tubes 26, solenoid 68, ultraviolet lamp 78, ultraviolet lamp holder 76, first motor 56 and second motor 54.

Top plate 14, base plate 12 and side plate 38 are connected together by support rods 36 and mechanical fasteners such as screws 88. It shall be appreciated that the shape and size of plates 12, 14, 38 may vary. It one embodiment, side plate 38 is transparent. Although the figures depict one side plate 38, any number of side plates may be used instead, which may or may not be transparent.

Top plate 14 comprises dispensing slot 16, which permits writing instrument 122 to pass through, either into or out of writing instrument storage apparatus 10. In one embodiment, motion sensor 42 and vector board 44 are secured to side plate 38 by using vector board screws 94 and vector board spacers 116. Motion sensor 42 is configured to enable the operation of instrument storage apparatus 10, which will be described in more detail later. Base plate 12 supports the weight of writing instrument storage apparatus 10 and is disposed on a flat surface such as a table. In one embodiment, bumper feet 118 are secured to the bottom of base plate 12 to enhance grip and prevent the apparatus from sliding on the flat surface. Bumper feet 118 may be made from any materials known in the field such as rubber.

A support assembly configured to store writing instruments 122 is disposed within the housing and rotatably mounted to base plate 12. The support assembly comprises carousel top 46, carousel divider 24, carousel base 20 and carousel gear 40. Carousel top 46, carousel divider 24, carousel base 20 and carousel gear 40 are secured together and fastened to base plate 12 by dowel pin 108 and pin spacer 110. It shall be appreciated that any additional fasteners such as screws may be used too. Transparent tubes 26 are placed within different compartments created by carousel divider 24, carousel top 46 and carousel base 20. Carousel top 46 comprises a plurality of openings that are aligned with the top ends of transparent tubes 26. This permits each writing instrument 122 to pass through dispensing slot 16 of top plate 14, an opening in carousel top 46 and the corresponding transparent tube 26 positioned beneath. Each transparent tube 26 comprises a metallic ball 120 disposed therein. Metallic ball 120 contacts any writing instrument 122 that is disposed within transparent tube 26.

A first motor assembly comprising first motor 56 and lift arm 28 is secured to side plate 38. More specifically, first motor 56 is secured to side plate 38 by first motor screws 84 and first motor spacers 98. Lift arm 28 comprises detent nub 30, magnet slot 32 and insert slot 34. Lift arm insert 48 is disposed within insert slot 34 of lift arm 28. Lift arm 28 is secured to first motor 56 by lift arm washer 106 and lift arm screw 90, which is inserted through lift arm 28, lift arm insert 48 and first motor 56. Magnet 72 is coupled to magnet slot 32 of lift arm 28. Detent nub 30 of lift arm 28 is configured to detachably couple with detent nub slot 52 of mount brace 50, which is disposed within writing instrument storage apparatus 10. As will be described in more detail later, first motor 56 is configured to pivotably adjust lift arm 28 to permit a particular writing instrument 122 stored within transparent tube 26 to push out of top plate 14 through dispensing slot 16.

Figure 4:
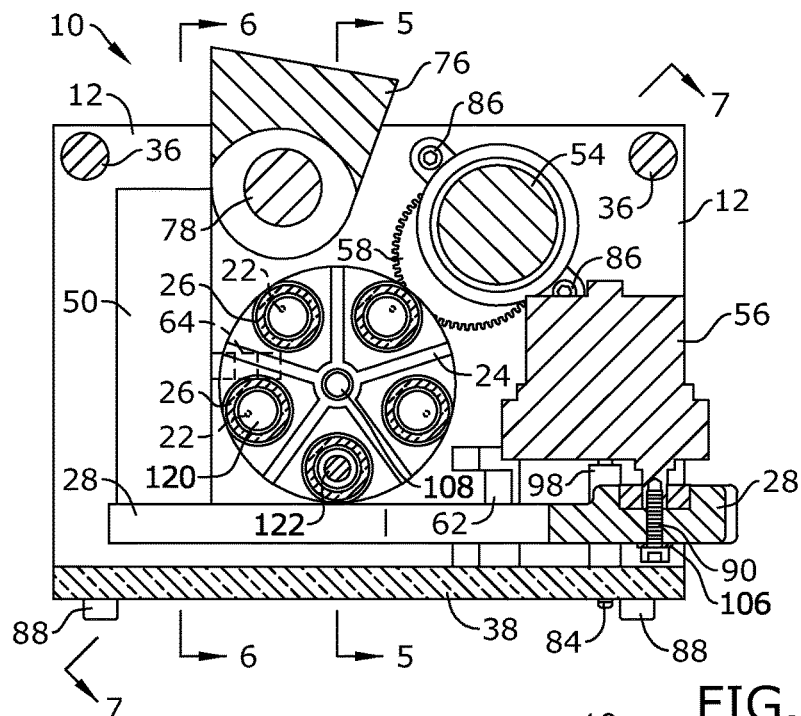
FIG. 4 depicts a section view of certain embodiments of the writing instrument storage apparatus taken along line 4-4 in FIG. 1.
Figure 5:
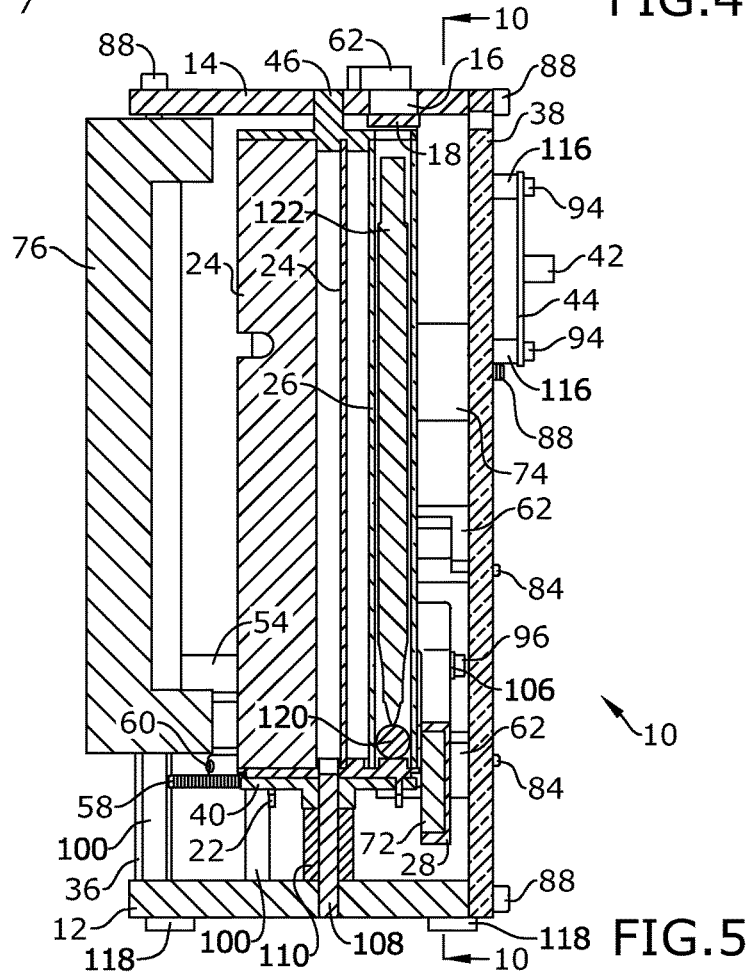
FIG. 5 depicts a section view of certain embodiments of the writing instrument storage apparatus taken along line 5-5 in FIG. 4.
Figure 6:
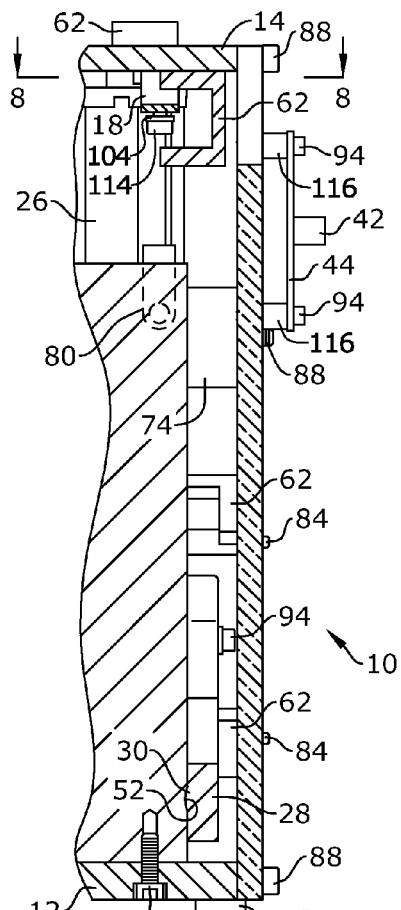
FIG. 6 depicts a section view of certain embodiments of the writing instrument storage apparatus taken along line 6-6 in FIG. 4.
Figure 7:
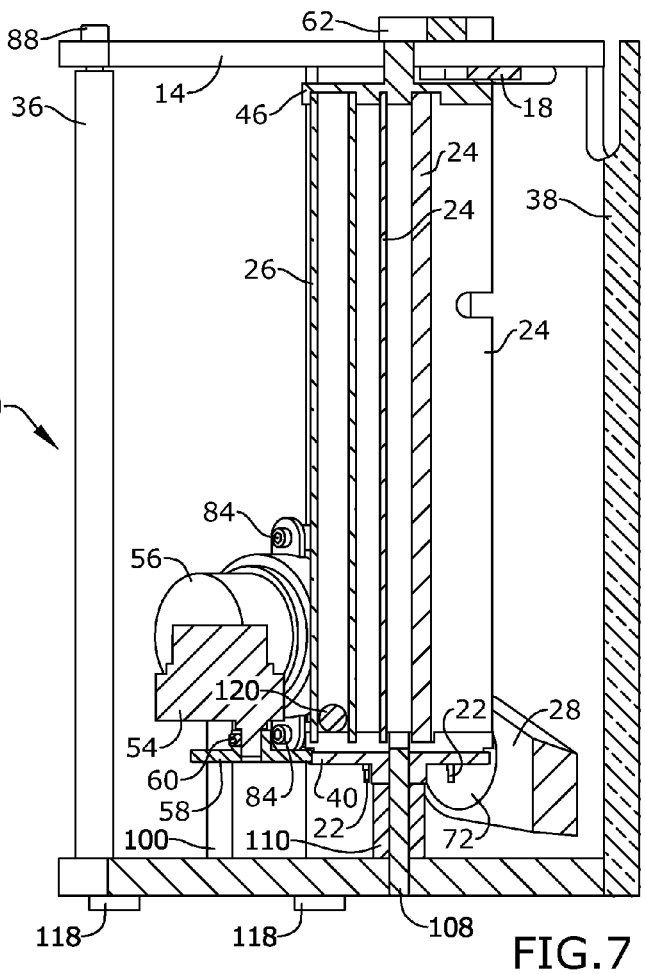
FIG. 7 depicts a section view of certain embodiments of the writing instrument storage apparatus taken along line 7-7 in FIG. 4.

A second motor assembly comprising second motor 54 and motor gear 58 is coupled to base plate 12 by using second motor screws 86 and second motor spacers 100. Motor gear 58 is rotatably mounted to second motor 54 by motor screw 60. Second motor 54 is configured to rotate motor gear 58 when activated. As depicted in FIGS. 4-5 motor gear 58 is mechanically coupled to carousel gear 40. As a result, this engagement causes motor gear 58 to drive carousel gear 40 to rotate transparent tubes 26 and any writing instruments 122 stored therein as needed.

Figure 8:
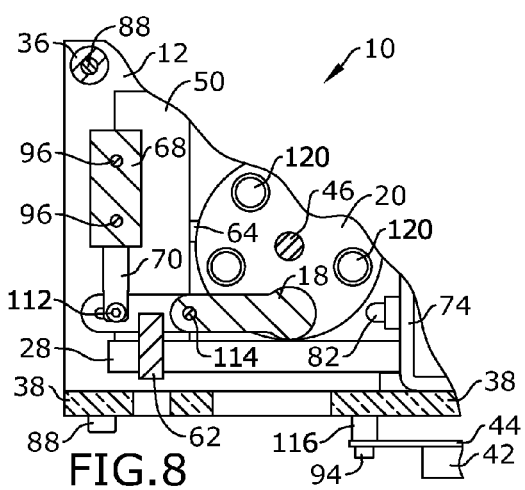
FIG. 8 depicts a section view of certain embodiments of the writing instrument storage apparatus taken along line 8-8 in FIG. 6.
Figure 9:
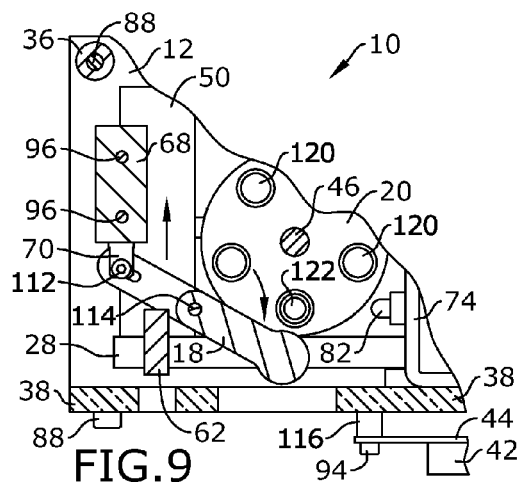
FIG. 9 depicts a section view of certain embodiments of the writing instrument storage apparatus.

In certain embodiments, additional components are used to control the operation of writing instrument storage apparatus 10 as depicted in FIGS. 6-11. In one embodiment, solenoid 68 comprising solenoid arm 70 is coupled to the interior face of top plate 14 by solenoid screws 96. Slot cover arm 18 is secured to top plate 14 by slot cover arm washer 104 and slot cover arm shoulder screw 114. An end of slot cover arm 18 is pivotably mounted to solenoid arm 70 by solenoid arm nuts 92, solenoid arm washers 102 and solenoid arm shoulder screws 112. Solenoid 68 is configured to adjust slot cover arm 18 to cover dispensing slot 16 of top plate 14 and a corresponding opening of transparent tube 26 beneath as depicted in FIG. 8. Alternatively, solenoid 68 is configured to adjust slot cover arm 18 to open cover dispensing slot 16 of top plate 14 and a corresponding opening of transparent tube 26 beneath as depicted in FIG. 9.

In one embodiment, photo transistor 82 is coupled to the interior of side plate 38 by bracket 74 and one or more screws 88. Photo transistor 82 is configured to help the apparatus determine whether any particular transparent tube 26 contains a writing instrument 122 stored therein. In one embodiment, light emitting diode emitter 80 is coupled to the exterior of mount brace 50. Light emitting diode emitter 80 is configured to display any colored lights and flashing patterns to alert a user of the operating status of writing instrument storage apparatus 10.

Figure 11:
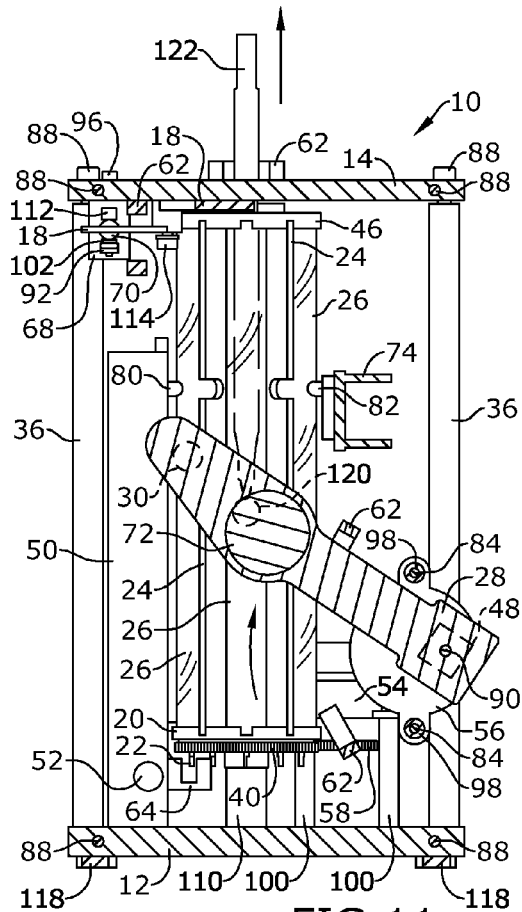
FIG. 11 depicts a section view of certain embodiments of the writing instrument storage apparatus.

In certain embodiments, small photo interrupter sensor 64 and a plurality of large photo interrupter sensors 62 are used to control the operation of writing instrument storage apparatus 10. In an exemplary configuration, a first large photo interrupter sensor 62 secured within the housing detects the position of slot cover arm 18, a second large photo interrupter sensor 62 coupled to top plate 14 around an edge of dispensing slot 16 determines when writing instrument 122 is ready to be disposed through dispensing slot 16, and a pair of large photo interrupter sensors 62 secured within the housing detects the position of lift arm 28. In one embodiment, small photo interrupter sensor 64 detects the position of carousel base 20. As depicted in FIGS. 3 and 11, carousel base 20 comprises a plurality of carousel base sensor pins 22 disposed throughout the outer edge. Small photo interrupter sensor 64 determines when one of the base sensor pins 22 passes through or is positioned within the sensor. As a result, the position of carousel base 20 can be determined as needed.

It shall be appreciated that any logic/circuit boards, processors and wiring (not shown) known in the field may be used to connect the components of writing instrument storage apparatus 10 together. Various power sources (not shown) may be used to power the components of the apparatus. In one embodiment, any type and number of batteries may be disposed within the housing. Alternatively, the apparatus may be connected to an external power outlet.

The logic/circuit boards and/or processors may be programmed to operate in a variety of ways. However, in one exemplary configuration, writing instrument storage apparatus 10 is operated as follows. A user places writing instrument 122 that is to be stored and sanitized above dispensing slot 16 on top plate 14. Large photo interrupter sensor 62 on top plate 14 determines the presence of writing instrument 122 in this position and signals solenoid 68 to adjust slot cover arm 18 to open dispensing slot 16 and a corresponding opening of transparent tube 26 beneath as depicted in FIG. 9. The user drops writing instrument 122 through dispensing slot 16 and the corresponding transparent tube 26 below. Once writing instrument 122 passes through dispensing slot 16 as determined by another large photo interrupter sensor 62 positioned nearby, solenoid 68 adjusts slot cover arm 18 to cover dispensing slot 16 of top plate 14. Second motor 54 is activated to rotate carousel base 20 to permit writing instrument 122 to be exposed to light generated by ultraviolet lamp 78. Light from ultraviolet lamp 78 passes through transparent tube 26 and contacts writing instrument 122, which sanitizes the instrument.

This process is repeated as many times as desired until all of transparent tubes 26 are filled with writing instruments 122 and sanitized by ultraviolet lamp 78. Photo transistor 82 determines whether any particular transparent tube 26 contains a writing instrument stored therein. This information allows second motor 54 to rotatably adjust carousel base 20 such that an empty transparent tube, if available, is properly aligned below dispensing slot 16 to receive another writing instrument 122.

Figure 10:
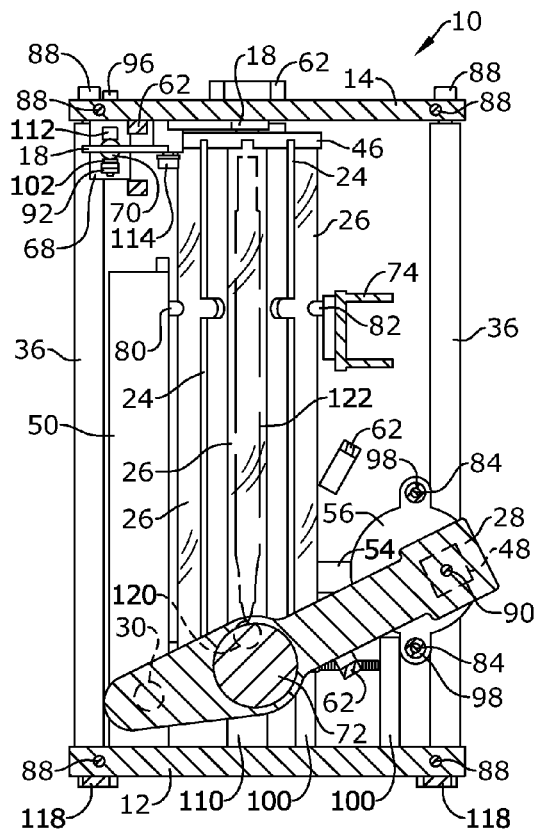
FIG. 10 depicts a section view of certain embodiments of the writing instrument storage apparatus taken along line 10-10 in FIG. 5.

To dispense a sanitized writing instrument, the user waves an object in front of motion sensor 42 on side plate 38. This causes second motor 54 to adjust carousel base 20 until a sanitized writing instrument stored within transparent tube 26 is aligned with dispensing slot 16 on top plate 14 as depicted in FIG. 10. In this position, lift arm 28 is in the rest position with detent nub 30 of lift arm 28 coupled to detent nub slot 52 of mount brace 50. Magnet 72 in lift arm 28 is positioned proximate metallic ball 120 in transparent tube 26. As a result, magnet 72 generates a force that attracts metallic ball 120. First motor 56 activates to pivot lift arm 28 to an upper position as depicted in FIG. 11. During this movement, magnet 72 attracts metallic ball 120 and causes the ball to slide up within transparent tube 26. As a result, metallic ball 120 pushes the sanitized writing instrument up, activates solenoid 68 to adjust slot cover arm 18 to open dispensing slot 16, and pushes the sanitized writing instrument through until a portion extends outside of the housing. Once the sanitized writing instrument is removed by the user, lift arm 28 returns to the lower rest position. A pair of large photo interrupter sensors 62 is configured to determine the position of lift arm 28, particularly in the upper and lower rest positions.

It shall be appreciated that the components of writing instrument storage apparatus 10 described in several embodiments herein may comprise any alternative known materials in the field and be of any color, size and/or dimensions. It shall be appreciated that the components of writing instrument storage apparatus 10 described herein may be manufactured and assembled using any known techniques in the field.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. An automated writing instrument storage apparatus configured to receive, sanitize and dispense a writing instrument with enhanced efficiency and reduced user effort, the storage apparatus comprising:
   a housing member comprising a top face, a bottom face and side faces, the top face comprising a slot sufficiently large to permit the writing instrument to pass therethrough;
   a support assembly disposed within the housing member and comprising a transparent tubular member generally aligned with the slot in the top face of the housing member and configured to receive the writing instrument;
   an ultraviolet lamp disposed within the housing member and configured to direct light generated by the lamp through the transparent tubular member to sanitize the writing instrument stored therein; and
   a motor assembly disposed within the housing member and operably connected to the support assembly, wherein the motor assembly is configured to activate to permit the sanitized writing instrument to slide within the transparent tubular member and through the slot of the housing member, thereby dispensing the sanitized writing instrument to a user;
   a metallic ball slidably mounted within the transparent tubular member, wherein the received writing instrument contacts the metallic ball.

2. The writing instrument storage apparatus of claim 1, wherein the motor assembly comprises a first motor, an arm pivotably mounted to the first motor, and a magnet coupled to the arm and configured to generate a force to attract the metallic ball, wherein pivotal movement of the arm upon activation of the first motor permits the metallic ball to slide within the transparent tubular member, thereby pushing the sanitized writing instrument through the slot in the housing member.

3. The writing instrument storage apparatus of claim 2, wherein the support assembly comprises a rotatable base member configured to store a plurality of transparent tubular members, each transparent tubular member in the plurality of transparent tubular members configured to align with the slot in the housing member to receive one of a plurality of writing instruments, each transparent tubular member comprising one of a plurality of metallic balls slidably mounted within the transparent tubular member that contacts the one of the plurality of writing instruments.

4. The writing instrument storage apparatus of claim 3, further comprising a second motor assembly disposed within the housing member and comprising a first gear, the first gear being mechanically coupled to a second gear coupled to the rotatable base member, wherein the second motor assembly is configured to rotate the first and second gears, thereby permitting the plurality of writing instruments stored within the transparent tubular members to be exposed to light from the ultraviolet lamp, wherein the second motor assembly is configured to rotate the first and second gears to align one of the plurality of transparent tubular members with the slot in the housing member.

5. The writing instrument storage apparatus of claim 4, wherein the magnet of the motor assembly generates a force to attract the metallic ball of the aligned one of the plurality of transparent tubular members, wherein pivotal movement of the arm of the motor assembly upon activation permits the metallic ball of the aligned one of the plurality of transparent tubular members to slide within the tubular member, thereby pushing the one of the plurality of writing instruments through the slot in the housing member.

6. The writing instrument storage apparatus of claim 5, further comprising a solenoid disposed within the housing member and coupled to a cover arm, wherein the solenoid is configured to adjust the cover arm to a first position to close the slot of the housing member, wherein the solenoid is configured to adjust the cover arm to a second position to open the slot of the housing member, thereby enabling the one of the plurality of writing instruments to pass therethrough.

7. The writing instrument storage apparatus of claim 6, further comprising a plurality of photo interrupter sensors operably connected to the storage apparatus, wherein a first photo interrupter sensor detects a position of the cover arm, wherein a second photo interrupter sensor detects a position of the rotatable base member, wherein a third photo interrupter sensor detects a position of the first motor assembly arm.

8. The writing instrument storage apparatus of claim 7, further comprising a motion sensor coupled to an exterior portion of the housing member, wherein the motion sensor is configured to enable the motor assembly.

9. The writing instrument storage apparatus of claim 8, further comprising at least one light emitting diode coupled to the housing member and configured to alert the user of a status of the storage apparatus.

* * * * *